United States Patent [19]

Cloke

[11] Patent Number: 5,548,044
[45] Date of Patent: Aug. 20, 1996

[54] POLYMERIZATION CATALYSTS

[75] Inventor: Frederick G. N. Cloke, Brighton, England

[73] Assignee: BP Chemicals Limited, London, England

[21] Appl. No.: 488,191

[22] Filed: Jun. 7, 1995

Related U.S. Application Data

[62] Division of Ser. No. 402,635, Mar. 13, 1995.

[30] Foreign Application Priority Data

Mar. 15, 1994 [GB] United Kingdom ............... 9405012

[51] Int. Cl.$^6$ ............................. C08F 4/642; C08F 4/68
[52] U.S. Cl. .................. 526/127; 526/126; 526/129; 526/901; 526/904; 526/348.5; 526/352
[58] Field of Search ................... 526/126, 160, 526/170, 127

[56] References Cited

U.S. PATENT DOCUMENTS 3,932,477  1/1976  Schrock .................................. 556/30
5,369,196  11/1994  Mateimoto et al. .................... 526/127

OTHER PUBLICATIONS

F. G. N. Cloke et al. (1994) JCS Chem Commun. 1207–8.
W. Kaminsky, SP '92 Polyethylene World Congress Dec. 7–9, 1992 '"Metallocene Catalysts".

Primary Examiner—Mark Nagumo
Attorney, Agent, or Firm—Brooks Haidt Haffner & Delahunty

[57] ABSTRACT

Novel Group IV or V metal complexes comprise cyclooctatetraene ligands. The complexes are suitable for use as catalysts for the polymerisation of olefins and may be supported for use in the gas phase.

A preferred complex has the formula:

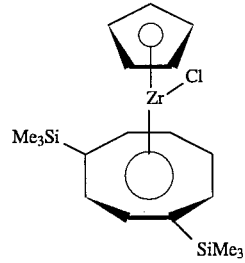

4 Claims, 1 Drawing Sheet (Zr(COT''')Cp Cl)

(Zr(COT''')Cp* Cl)

(Ta(COT''')Me₃)

FIGURE
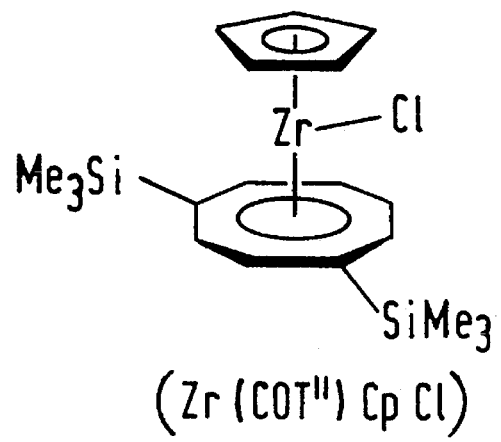
(Zr(COT")Cp Cl)
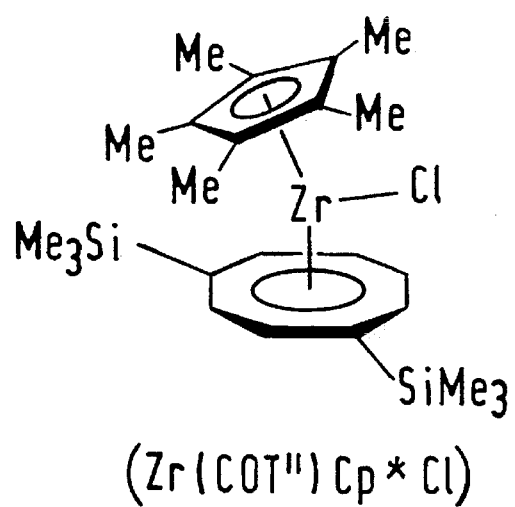
(Zr(COT")Cp*Cl)
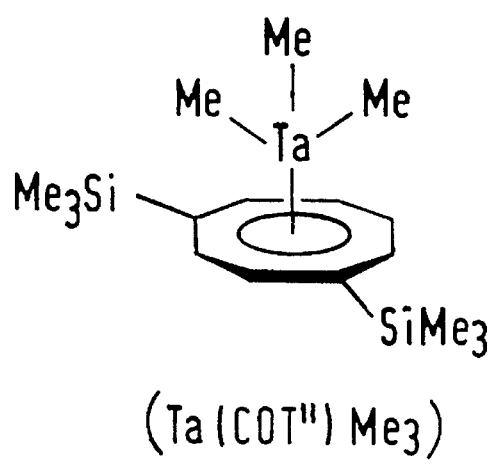
(Ta(COT")Me₃)

POLYMERIZATION CATALYSTS

This application is a division of application Ser. No. 08/402,635 filed on Mar. 13, 1995.

The present invention relates to novel cyclooctatetraene complexes of Group IV and V metals and to their use as olefin polymerisation catalysts.

Catalysts comprising transition metals have been widely used for the polymerisation of olefins. For example bis (cyclopentadienyl)metal complexes containing zirconium or titanium have long been recognised as an important class of catalysts for the Ziegler-Natta polymerisation of olefins.

More recently substituted cyclopentadienyl metal complexes, in particular those based on zirconium, have been found to be particularly active as catalysts. Such catalysts, referred to as metallocenes, may be used to produce polyolefins with a wide range of properties. Examples of metallocene catalysts may be found in EP129368 or EP206794.

We have now found that certain novel transition metal complexes having cyclooctatetraene groups may be prepared and used as catalysts or catalyst precursors for the polymerisation of olefins.

Thus according to a first aspect of the invention there is provided a novel transition metal complex having formula I or II:

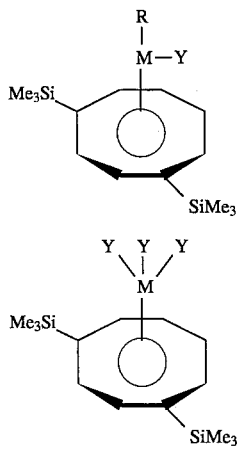

wherein

Y is halide, hydride or a hydrocarbyl group having from 1 to 20 carbon atoms and may be the same or different, R is an unsubstituted or substituted cyclopentadienyl ring, and in Formula I M is Zr, Ti or Hf and in Formula II M is tantalum, vanadium or nobium Preferred complexes are those in which:

M is zirconium or tantalum,

Y is chlorine or methyl.

A particularly preferred complex is:

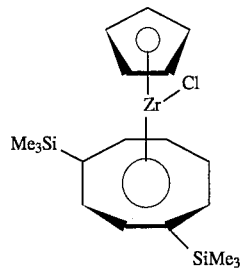

In Formula I the cyclopentadienyl ring may conveniently be substituted by hydrocarbyl groups having 1 to 20 carbon atoms or two substituents may together form a fused ring.

Examples of complexes according to the present invention are shown in the accompanying Figure.

The complexes according to the present invention may suitably be prepared from 1,4-di(trimethylsilyl) cyclooctatetraene. Experimental procedures for the preparation of selected complexes are given in detail below in the Examples.

The novel complexes according to the present invention may be used in catalysts compositions for the polymerisation of olefins in particular for the polymerisation of ethylene.

The complexes may be used in the presence of suitable co-catalysts for example organometallic compounds having a metal from Group IA, IIA, IIB or IIIB of the Periodic Table.

Such co-catalysts are well known for their use in the polymerisation of olefins. Examples include organoaluminium compounds such as trimethylaluminium or triethylaluminium, alkyl alkoxy aluminium compounds or partially hydrated aluminium alkyls such as aluminoxanes.

A preferred co-catalyst is methyl aluminoxane (MAO) and commercial materials known as modified MAO (MMAO).

The co-catalyst may be mixed with the complex optionally on an inorganic support. Alternatively, the co-catalyst may be added to the polymerisation medium along with the complex. The co-catalyst eg MAO may also be prepared in-situ by pretreating the support with for example trimethyl aluminium or other alkyl aluminium. Suitably, the amount of co-catalyst mixed with complex may be such as to provide an atom ratio of M from the complex to the metal in the co-catalyst of 1 to 10,000:10,000 to 1 for aluminoxanes and 1 to 100:100 to 1 otherwise.

The complex may suitably be supported on a suitable inorganic support material.

Any suitable inorganic support may be used for example, inorganic oxides such as silica, alumina. Equally suitable inorganic halides may be used. Suitable halides include Group IIA halides eg magnesium chloride.

A preferred inorganic support is silica

The complex may be impregnated onto the support material under anhydrous conditions and under an inert atmosphere. The impregnation can be conducted using an inert solvent, in which case the solvent may then be evaporated under reduced pressure. The impregnated support may then be heated to remove any remaining solvent. The complex and co-catalyst may be dissolved in the inert solvent. Suitable inert solvents include aromatic hydrocarbons, such as toluene. The solution of complex and co-catalyst may then be added to the inorganic support material.

Other suitable means of forming a supported polymerisation catalyst may also be used.

The olefin polymerisation catalyst compositions comprising the complexes according to the present invention may be used to produce polymers using solution polymerisation, slurry polymerisation or gas phase polymerisation techniques. Methods and apparatus for effecting such polymerisation reactions are well known and described in, for example, Encyclopaedia of Polymer Science and Engineering published by John Wiley and Sons, 1987, Volume 7, pages 480 to 488 and 1988, Volume 12, pages 504 to 541. The catalyst compositions may be used in similar amounts and under similar conditions to known olefin polymerisation catalysts.

Thus according to another aspect of the present invention there is provided a process for the production of polyolefins, in particular homopolymers of ethylene and copolymers of ethylene with minor amounts of at least one C3 to C 10, preferably C3 to C8 alpha-olefin. The process comprises contacting the monomer or monomers, optionally in the presence of hydrogen, with a catalyst comprising a complex of formula I or II in an olefin polymerisation catalyst composition according to the above aspects of the present invention at a temperature and pressure sufficient to initiate the polymerisation reaction.

The complexes according to the present invention may also be used in multisite catalyst systems together with known polymerisation catalysts eg Ziegler catalysts. Alternatively the multisite catalyst may comprise two different complexes according to the present invention.

Suitably the alpha olefin may be propylene, butene-1, hexene-1, 4-methyl pentene-1 and octene-1 and may be present with the ethylene in amounts of 0.001–80% by weight (of the total monomers). The polymers or copolymers of ethylene thus obtained can have densities, in the case of homopolymers of about 950 to 960 or 965 or in the case of copolymers, as low as 915 kg/m$^3$ or even lower eg less than 900 kg/m$^3$. The C3 to C8 alpha-olefin content in the copolymers of ethylene can be about from 0.01% to 10% by weight or more.

The polymerisation may optionally be carried out in the presence of hydrogen. Hydrogen or other suitable chain transfer agents may be employed in the polymerisation to control the molecular weight of the produced polyolefin. The amount of hydrogen may be such that the percentage of the partial pressure of hydrogen to that of olefin(s) is from 0.01–200%, preferably from 0.05–10%.

Typically, the temperature is from 30° to 110° C. for the slurry or "particle form" process or for the gas phase process. For the solution process the temperature is typically from 60° to 250° C. The pressure used can be selected from a relatively wide range of suitable pressures, eg from subatmospheric to about 350 MPa. Suitably, the pressure is from atmospheric to about 6.9 MPa, or may be from 0.05–10, especially 0.14 to 5.5 MPa. In the slurry or particle form process the process is suitably performed with a liquid inert diluent such as a saturated aliphatic hydrocarbon. Suitably the hydrocarbon is a C4 to C10 hydrocarbon, eg isobutane or an aromatic hydrocarbon liquid such as benzene, toluene or xylene. The polymer is recovered directly from the gas phase process or by filtration or evaporation from the slurry process or evaporation from the solution process.

The complex according to the present invention may suitably be employed in the form of a prepolymer prepared beforehand during a prepolymerisation step. The prepolymerisation may be carried out by any suitable process, for example polymerisation in a liquid hydrocarbon diluent or in the gas phase using a batch process, a semi-continuous process or a continuous process.

Another feature of the present invention relates to novel cyclooctatetraene complexes as precursors of the complexes described above. In particular the following novel complexes are disclosed:

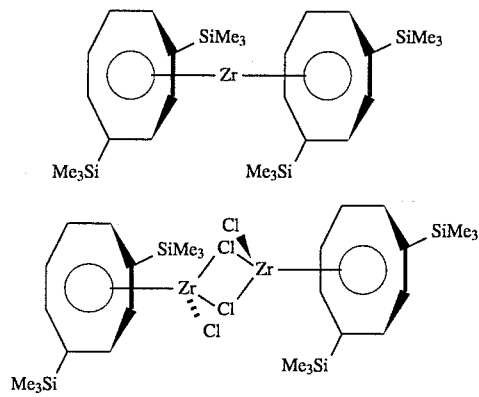

The present invention will now be further illustrated by reference to the following examples which describe the preparation of cycloctatetraene complexes according to the present invention. In the examples the following abbreviations are used:

COT"=1,4-bis(trimethylsilyl) cyclooctatetraene
Cp=cyclopentadiene
Cp*=pentamethylcyclopentadiene
Cp'=methylcyclopentadiene
TMA=trimethylaluminium
MAO=methyl aluminoxane
MMAO=modified MAO

PREPARATION OF COMPLEXES

Experimental

General Procedures

All manipulations were conducted in a inert atmosphere of argon or dinitrogen. This was achieved using a dual vacuum/argon (or dinitrogen) line, employing conventional Schlenk line techniques, or in either a Miller-Howe glove box under an atmosphere of dinitrogen (<5 ppm $H_2O$,<2 ppm $O_2$) or a Braun glove box (<2 ppm $H_2O$,<1 ppm $O_2$). All solvents were pre-dried by distillation under dinitrogen over the appropriate drying agent; toluene (sodium), 40–60 petroleum ether and pentane (sodium potassium alloy), diethyl ether (potassium) and subsequently degassed and stored in glass ampoules under argon in the presence of a sodium (or potassium) mirror. All glassware, cannulae and Celite were stored in an oven (>373° K.) and glassware and Celite were flame-dried in vacuo immediately prior to use. Unless otherwise stated, all reagents and chemicals were purchased from the Aldrich Chemical Co. and used without further purification. Deuteriated solvents were purchased from M.S.D. Isotopes, Ltd. They were degassed by the freeze-thaw method, refluxed in vacuo over molten potassium or sodium (according to boiling point) and then vacuum transferred to a glass ampoule fitted with Young's tap prior to storage in the glove box.

(COT")$_2$Hf$_2$Cl$_2$ and its precursors were prepared employing identical procedures used for analogous Zr complexes.

NaCp, NaCp*, $ZrCl_4(THF)_2$ and Cp'MgCl were prepared according to published procedures.

EXAMPLE 1

Preparation of COT"$H_2$

To a pentane (100 mL) solution of cyclooctadiene (12.3 mL 100 mmol) at 0° C. was added n BuLi (120 mL, 2.5M in hexanes, 300 mmol) dropwise over a period of 20 min. Once the addition was complete tetramethylethylenediamine (45.2 mL, 300 mmol) was added dropwise. After an initial thickening of the mixture the suspension dissolved to afford a deep red solution which was then stirred at ambient temperature overnight after which time an orange solid precipitated from the solution. The reaction mixture was refluxed for 24 h then cooled to −30° C. Trimethylsilyl chloride (45 mL, 350 mmol) was added dropwise and the reaction mixture was slowly warmed to ambient temperature and stirred overnight. The reaction was quenched in ice water. The pale yellow organic phase was separated and washed with water and dried over magnesium sulphate. Removal of all volatiles in vacuo afforded a yellow oil. Addition of methanol and cooling to −30° C. induced crystallization of the product. A white crystalline solid was isolated and stored at −30° C. Yield 17.2 g (68%).

EXAMPLE 2

Synthesis of COT"$Li_2(THF)_x$ 1,4-di(trimethylsilyl)cyclooctatetraene, (10 g, 40 mmol) was added to THF (30 mL). The solution was cooled to −78° C. BuLi (32 mL, 80 mmol, 2.5 M solution in hexanes) was added via cannula over the course of 20 min. The reaction suspension was warmed to ambient temperature and stirred for 1 hr. All volatiles were removed in vacuo. The vessel was placed into an oil bath at 60°–70° C. and vacuum was applied for 6 h. After cooling, pentane (150 mL) was added to the solid and the resulting suspension was stirred for 1.5 h, then cooled to −50° C. for 2 h. The solid was isolated by vacuum filtration and subsequently dried in vacuo. Yield 12 g (depending on x) ca. 92%, and x is usually between 1 and 2.

EXAMPLE 3

Synthesis of COT"$_2$Zr

To a colourless THF (30 mL) solution of $ZrCl_4(THF)_2$ (0.57 g, 1.5 mmol) at 0° C. was added a THF (30 mL) solution of $Li_2COT$" (1.0 g, 3.2 mmol) dropwise over 1 h. After completed addition the purple solution was allowed to stir at room temperature overnight. The solvent was removed in vacuo to afford a purple oil, subsequently dissolved in petroleum ether (40–60) and filtered through Celite to remove LiCl. The combined filtrates were concentrated and placed in a freezer at −30° C. for 3 days to afford the product as purple crystals. Yield 0.53 g (58%).

EXAMPLE 4

Synthesis of (COT")$_2$Zr$_2$Cl$_4$

A round bottomed flask fitted with a reflux condenser and gas inlet was charged with $ZrCl_4(THF)_2$ (0.48 g, 1.27 mmol) and Zr(COT")$_2$ (0.75 g, 1.27 mmol). Toluene (60 mL) was added to afford a purple solution. This solution was refluxed overnight in a sealed high pressure ampoule. The reaction mixture was filtered through Celite and the combined filtrates concentrated to dryness. Yield 0.98 g (95%).

EXAMPLE 5

Synthesis of COT"CpZrCl

To a solid mixture of (COT")$_2$Zr$_2$Cl$_4$ (0.5 g, 0.61 mmol) and NaCp (0.11 g, 1.25 mmol) placed in a high pressure ampoule was added toluene (40 mL) via cannula at ambient temperature. A green colouration formed immediately and some warming of the reaction vessel was evident. The ampoule was partially evacuated, sealed with a rotoflow tap, and heated to ca. 130° C. overnight during which time the green colour of the solution became more intense. Some white precipitate (presumably NaCl) was also observed in the reaction mixture. The contents of the ampoule were transferred to a Schlenk flask and toluene was removed in vacuo to afford an oily green residue. This was heated to 60° C. in vacuo for 2 h to remove traces of solvent. The green solid was scraped down from the walls of the Schlenk flask in the glove box and transferred to a sublimer tube. The solid (initially melting at ca. 100° C. in vacuo) was then sublimed (150° C./1×10$^{-6}$ mm Hg) to afford the pure product as an intense yellow microcyrstalline solid. Yield 0.28 g (52%).

EXAMPLE 6

Synthesis of COT"Cp'ZrCl

To a solid mixture of COT"$_2$Zr$_2$Cl$_4$ (1 g, 1.2 mmol) and $(C_5H_4Me)MgCl(Et_2O)_{1.27}$ (0.56 g, 2.4 mmol) placed into a high pressure ampoule was added toluene (40 mL) at −10° C. via cannula. A yellow colouration formed immediately. The ampoule was then partially evacuated and the contents heated to 120° C. overnight during which time the suspension turned green. The toluene was removed in vacuo to afford an oily green residue. The residue was extracted into pentane (100 mL) and then filtered through a glass frit covered with Celite. The pentane was removed in vacuo. The remaining solid was dissolved in diethyl ether (30 mL), concentrated and cooled to 0° C. affording a yellow crystalline solid. Yield 60% (not optimised).

EXAMPLE 7

Synthesis of COT"Cp*ZrCl

The preparation follows an analogous procedure used for COT"CpZrCl. The following quantities were used: (COT")$_2$Zr$_2$Cl$_4$ (0.50 g, 0.61 mmol) and NaCp* (0.192 g, 1.22 mmol). Purification via sublimation (160° C./10$^{-5}$ mm Hg) over 6 h afforded the product as a bright yellow micro crystalline solid. Yield 0.31 g (50%).

EXAMPLE 8

Synthesis of COT"CpHfCl

The preparation follows an analogous procedure used for COT"CpZrCl, except that following the overnight reflux of (COT")$_2$Hf$_2$Cl$_2$ (1.0 g, 1.0 mmol) and NaCp (0.18 g, 2.0 mmol) the solvent was removed in vacuo and the residue extracted with petroleum ether (40–60), filtered through Celite, and concentrated to ca. 10 mL. Cooling to −30° C. overnight led to the precipitation of the product as a pale orange powder. Yield 0.34 g (64%).

EXAMPLE 9

Synthesis of COT"CpZrMe

COT"CpZrCl (2.7 g, 6.1 mmol) was added to diethyl ether (100 mL) while stirring. The yellow solution was cooled to −78° C. and MeLi (4.4 mL, 6.1 mmol, 1.4M solution in diethyl ether) was added via syringe. After completed addition the reaction mixture was slowly warmed and stirred for 2 h at ambient temperature. All volatile were removed in vacuo. Pentane (100 mL) was added and the mixture was filtered through a glass frit covered with Celite. The solvent was removed from the filtrate in vacuo until ca. 5 mL remained. This was cooled to −50° C. for 3 h after which the supernatant fluid was removed via filter cannula. The solid was washed with pentane (5 mL). Yield=1.5 g (58%).

EXAMPLE 10

Synthesis of COT"CpZrEt

To a mixture of COT"CpZrCl (1.5 g, 3.4 mmol) and solid EtMgBr(MeOCMe$_3$)$_{0.5}$ (0.62 g, 3.4 mmol) diethyl ether (20 mL) was added at −93° C. while stirring. The reaction mixture was warmed slowly to ambient temperature yielding brown suspension which was stirred overnight. All volatile were removed in vacuo and pentane (20 mL) was added. The suspension was filtered through a glass frit covered with Celite. Dioxane (2 mL) was added to the filtrate, leading to the formation of a precipitate. This was removed by vacuum filtration through a glass frit covered with Celite. Dioxane was added to the filtrate which was filtered through Celite again. The filtrate (ca. 10 mL) was cooled to −50° C. for 2 days. After briefly warming to RT a yellow crystalline solid was isolated by decantation. Yield: 0.5 g (35%).

EXAMPLE 11

Synthesis of TaCl$_2$Me$_3$

To a pentane (50 mL) suspension of TaCl$_5$ (3.58 g, 10 mmol) at 0° C. was added a pentane (20 mL) solution of ZnMe$_2$ (1.57 g, 16.5 mmol) dropwise during which time a milky-white suspension formed. After the addition was complete, the reaction mixture was stirred overnight at ambient temperature. The cloudy-grey reaction mixture was filtered through Celite and the yellow filtrates collected at 0° C. The filtrates were pumped dry in vacuo at 0° C. and the yellow solid that remained was sublimed onto a liquid nitrogen cooled cold finger. The apparatus was transferred to the glove-box where the product was scraped down and quickly weighed. Yield 2.5 g (85%).

EXAMPLE 12

Synthesis of COT"TaMe$_3$

To a pentane (40 mL) solution of TaCl$_2$Me$_3$ (0.25 g, 0.84 mmol) at −40° C. was added a pentane (40 mL) suspension of Li$_2$COT" (0.28 g, 0.90 mmol) dropwise over a period of 45 minutes during which time the colour of the reaction mixture darkened. Once the addition was complete the brown suspension was stirred at −40° C. for 60 min. before being warmed to room temperature and left to stir overnight. After this time the solution had deepened to a red colour and the presence of a white solid was observed. The solution was filtered through Celite and the filtrates were reduced to ca. 20 mL. Cooling the solution overnight to −30° C. led to the precipitation of the product as purple crystals. Yield 0.28 g (70%).

EXAMPLE 13

"One Pot" Synthesis of COT"$_2$Zr$_2$Cl$_4$

To a solid mixture of COT"Li$_2$(THF)$_{1.25}$ (10.0 g, 28.4 mmol) and ZrCl$_4$(THF)$_2$ (5.35 g, 14.2 mmol) diethylether (300 mL) was added and the resulting suspension stirred for 48 h at ambient temperature. All volatiles were removed in vacuo and the residue extracted with toluene and filtered through Celite. The filtrate was placed into an ampoule with ZrCl$_4$(THF)$_2$ ( 5.35 g, 14.2 mmol) and heated to 120° C. overnight. The reaction solution was filtered (filter cannula) and volatiles were removed in vacuo. The solid residue was washed with petroleum ether (40–60) and dried in vacuo. Yield 9.5 g (82%).

The present invention will be further illustrated by reference to the following examples which illustrate the preparation of supported catalysts comprising complexes prepared in the above examples.

Preparation of Supported Catalysts

All solid components were loaded into dry schlenk tubes in a N$_2$ glovebox. Toluene was distilled over sodium before use and thoroughly degassed. Silicas were calcined in a fluid bed under a flow of dry N$_2$.

EXAMPLE 14

A solution of MAO in toluene (Witco, 7 ml, 2.13M, 15 mmol Al) was added by syringe to a Schlenk containing COT"CpZrCl (44 mg, 0.1 mmol) under N$_2$. An additional 3 ml toluene was added to this solution. This solution was then added by cannula wire to a rapidly stirring ES70 silica (2 g, previously calcined at 800° C. and further dehydroxylated by trimethylaluminium treatment) under N$_2$ at 20° C. This slurry was stirred for 1 hour at 20° C., then the toluene was removed in vacuo at 40° C. for 3 hours to give a free flowing off-white solid.

EXAMPLE 15

A solution of MMAO in toluene (Akzo type 4, 6.25 ml, 2.4M, 15 mmol Al) was added by syringe to a Schlenk flask containing COT"CpZrCl (44 mg, 0.1 mmol) under N$_2$. An additional 2.5 ml toluene was added to this solution. This solution was then added by cannular wire to a rapidly stirring ES70 silica (2 g, previously calcined at 800° C.) under N$_2$ at 20° C. This slurry was stirred for 1 hour at 20° C., then the toluene was removed in vacuo at 40° C. for 50 minutes to give a free flowing off-white solid.

EXAMPLE 16

Zr(COT)"CpCl"(0.0711 g) was dissolved in 1.67M Witco MAO/toluene solution (16 ml). The solution was then added to Crosfield ES70 silica 5. (calcined to 800° C. for 5 hours under N$_2$, 2.18 g) at room temperature (about 200° C.) and stirred for 1 hour. The slurry was then pumped down with stirring until no more toluene could be removed.

EXAMPLE 17

COT'CpZrCl (0.033 g) was dissolved in toluene and added to Witco MAO solution in toluene (4.9 ml, 2.13M). This solution was added to 1.80 g of a silica supported Ziegler catalyst prepared as follows:

ES70 silica was slurried in hexane and hexamethyldisilazane (0.8 mM/g SiO$_2$) added with stirring. Dibutylmagnesium (1.5 mM/g SiO$_2$) was then added followed by t-butyl chloride (3 mM/g SiO$_2$). Finally an equimolar mixture of titanium tetrachloride and titanium tetra-n-butoxide (0.15+ 0.15 mM/g SiO$_2$) were added before the slurry was dried under a flowing N$_2$ stream.

The mixture of the supported catalyst and the COT"Cp ZrCl/MAO solution was stirred for 1 hour at room temperature before the toluene was removed by vacuum. The nominal composition of the catalyst was 1.03% w/w Ti, 0.28% w/w Zr with an Al/Zr ratio of 139:1.

EXAMPLE 18

7 ml of dry toluene was added to 44 mg of COT"CpZrCl. 7 ml of 2.13M MAO in toluene (Witco) was added to this solution (AL/Zr 150:1). The COT"CpZrCl/MAO/toluene solution was added to 2 g silica (ES70, heated at 800° C., $N_2$). During the addition the silica was stirred. A further 2 ml of toluene was then added. The slurry was stirred at 20° C. for 1 hour. The toluene was then removed under vacuum at 40° C. for 3 hours.

EXAMPLES 19–28

Polymerisations—Slurry Phase

Catalyst Evaluation

Catalyst evaluation was carried out in a stirred 3 L autoclave operated in slurry mode using isobutane solvent. Agitation was carried out using a paddle stirrer and heat exchange carried out via the autoclave jacket. Temperature was controlled using a cascade controller and data logging was carried out using a HP Vectra QS20 computer.

Before catalyst evaluation, the autoclave was cleaned, assembled and baked out by heating the autoclave to 95° C. and purging the vessel with dry $O_2$ free $N_2$ (>0.5 L/min) for 1 hour. The vessel was then cooled down under $N_2$ to about 40° C. and the manifold checked for tightness. The autoclave was then pressure tested and sealed under $N_2$ at atmospheric pressure. $N_2$ was then purged through the catalyst injection system until load-up.

Catalysts were evaluated with and without comonomer and $H_2$ using various cocatalysts. Comonomer 4 methyl pentene-1 distilled over Na metal, (50 ml) was added (optionally) via the catalyst injector. The MAO cocatalyst and cocatalyst combinations (when used) were then added and flushed into the reactor with isobutane (1.5 L). Agitation was then started and temperature brought to the set point (75° C.). The partial pressure of the reactor contents was then recorded and any $H_2$ (optionally) partial pressure added. A further 10 bar(g) of ethylene was then added to the reactor and temperature allowed to stabilise.

Data logging was started and the catalyst injection system purged with $N_2$. Catalyst solutions were then injected into the autoclave using $N_2$ overpressure (5 bar(g) above reactor contents). Polymerisation was allowed to continue for 1 hour, ethylene being taken up upon demand (via a constant pressure mass flow controller). After the test period, the ethylene gas was isolated, the reactor cooled, depressured and the polymer unloaded.

Polymer Evaluation

Polymers from autoclave runs were allowed to dry (removal of isobutane solvent) by degassing at ambient temperature. They were then weighed (to determine catalyst activity) and then washed to remove MAO residues. Polymers were slurried with an excess of methanol/HCl solution (made by adding 50 ml of HCl (conc) to methanol 2.5 liters), filtered and washed with 1:1 ethanol:water. The polymer was then dried at 40° C. (1 bar(abs) vacuum) and characterised.

EXAMPLES 29–36

Polymerisations—Gas Phase

A 3 liter autoclave was heated, whilst stirring, at 90° C. for 1 hour with a flow of 1–2 liter/min nitrogen purging the reactor. During this time the catalyst (normally 0.25 g) was added, under nitrogen, to a catalyst injector constructed from a non return valve and a ball valve. The catalyst was kept in a nitrogen atmosphere within the catalyst injector and attached to the autoclave in such a way as to purge any air from couplings. The reactor was cooled to below 50° C. and 300 g of predried sodium chloride added under nitrogen atmosphere. The NaCl (1 mm diameter) was dried at 150° C. under vacuum for a period greater than 4 hours. TMA (3 ml, 2M in hexanes) was added to the reactor under nitrogen at 50° C. The reactor was boxed in nitrogen at 1 atm and the temperature then increased to 80° C. The reactor was left, stirring, at 80° C. for greater than 20 minutes. The reactor was purged with nitrogen at 80° C. and then left with 1 bar nitrogen. The reactor temperature was adjusted to 3° C. below that which was to be used in the polymerisation. Hydrogen was added to the autoclave, if required, at this point. Ethylene and hexene-1 were then added. The catalyst was injected into the reactor at this steady state condition. The pressure of the reactor normally increased by 0.3 bar during the injection. After the catalyst had been added the reactor temperature was raised to the reaction temperature. The catalyst was tested for intervals between 30 minutes and 2 hours.

During the test ethylene was fed at the required rate to keep the total pressure of the autoclave constant whilst any hexene-1 comonomer or hydrogen addition was at a rate so as to keep the hexene-1/ethylene and hydrogen/ethylene ratios constant. The ratios were measured by the use of on-line mass spectral analysis of the gaseous reactor contents.

The reaction was terminated by venting off the reactant vapour, purging the autoclave with nitrogen and lowering of the temperature to 40° C. The polymers were washed with water, to remove the salt, and then acidified methanol (50 ml concentrated HCl) and finally ethanol/water (1:4 v/v). The washed polymer was dried in vacuo at 40° C.

In Example 31 the catalyst was tested as above except that 1 cm3 of TMA (2M in hexanes) was added, under nitrogen, to the autoclave at 50° C. after the four 4 bar nitrogen pressure purges. The reactor was again boxed in under nitrogen and the temperature raised to 77° C. Ethylene and hexene were added as previously.

In Example 33 the autoclave was heated to 80° C. prior to the addition of the sodium chloride. TMA was then added to the autoclave at 80° C. after the addition of the salt and boxed in $N_2$ for 90 minutes. The TMA was purged from the reactor under a $N_2$ flow at 75° C. The reactor was cooled to 40° C and a further 2 ml of 2M TMA in hexane was added. The reactor was boxed in $N_2$ at 1 bar (a) and heated to 73° C. Ethylene (8 bar) was added.

The catalyst was mixed with 1.1 g silica (ES70 predried at 800° C., $N_2$>5 hours) and injected under $N_2$ into the autoclave. Ethylene was added at a flow rate to keep the pressure of the autoclave constant.

Details of the polymers prepared using slurry or gas phase polymerisation procedures are given in the accompanying Tables 1 and 2 respectively.

TABLE 1

| Example | Complex | Co-Catalyst | Al:Zr Ratio | $C_2^=$ bar (g) | $H_2$ bar (g) | 4MP-1 (50 ml) | Mw/Mn | Activity g/mmol/Zr/hr/b$C_2^=$(1 hr) |
|---|---|---|---|---|---|---|---|---|
| 19 | A | MAO | 6000 | 10 | No | No | 2.5 | 2188 |
| 20 | A | MAO | 6000 | 10 | No | Yes | — | 750 |
| 21 | A | MAO | 6000 | 10 | No | No | — | 2122 |
| 22 | A | MAO | 6000 | 10 | No | No | 2.2 | 1263 |
| 23 | A | MAO | 6000 | 10 | 1.4 | No | 2.2 | 829 |
| 24 | A | MAO | 6000 | 10 | No | Yes | 2.5 | 1221 |
| 25 | A | MAO | 6000 | 10 | No | No | — | 115 |
| 26 | A | MAO/TEA | 6000 + 2000 | 10 | No | No | — | 130 |
| 27 | A | MAO/TMA | 6000 + 2000 | 10 | No | No | — | 673 |
| 28 | A | MAO | 6000 | 10 | No | No | — | 291 |

*all reactions carried out at 75° C.
A = COT"CpZrCl

TABLE 2

| Example | 32 | 33 | 34 | 35 | 36 | 37 | 38 | 39 |
|---|---|---|---|---|---|---|---|---|
| Catalyst | A | B | A | C | D | A | A | E |
| Wt Catalyst (g) | 0.249 | 0.252 | 0.249 | 0.25 | 0.537 | 0.508 | 0.499 | 0.442 |
| % w/w Zr | 0.31 | 0.31 | 0.31 | 0.31 | 0.31 | 0.31 | 0.31 | 0.28 |
| % w/w Ti | 0 | 0 | 0 | 0 | 0 | 0 | 0 | 1.03 |
| Temperature (°C.) | 80 | 80 | 80 | 80 | 75 | 85 | 90 | 80 |
| Ethylene (bar) | 8 | 8 | 8 | 8 | 8 | 8 | 8 | 8 |
| Hydrogen (bar) | 0 | 0 | 0 | 0 | 0 | 0 | 0 | 0.07 |
| Hexene-1 (cm³) (liquid added at start) | 1.2 | 1.2 | 1.2 | 1.2 | 0 | 1.2 | 1.2 | 1.2 |
| Time of Test (min) | 110 | 60 | 78 | 60 | 60 | 63 | 142 | 42 |
| Wt Polymer | 5.35 | 2.08 | 8.43 | 1.56 | 13.39 | 16.75 | 19.52 | 90.58 |
| Mw | 105900 | — | 68100 | — | — | — | — | — |
| Mn | 13900 | — | 9700 | — | — | — | — | — |

Catalyst A - prepared according to Example 18
Catalyst B - prepared according to Example 14
Catalyst C - prepared according to Example 15
Catalyst D - prepared according to Example 16
Catalyst E - prepared according to Example 17

EXAMPLES 37–42

The complexes according to the present invention will now be further illustrated with reference to a conventional metallocene catalyst ($Cp_2ZrCl_2$) (Example 37).

The following procedure was used.

All polymerisation studies were carried out using a stainless steel polymerisation rig. The monomer under study (ethylene) was of reagent grade (99.99%) and was passed first through molecular sieves and then over glass wool coated in potassium prior to exposure to the organometallic catalyst. Actual polymerisations were carried out in thick wall glass autoclaves attached to the rig via a stainless steel flange system that had been previously pressure tested to 20 atms. The autoclave and attachments were taken into a Miller-Howe glove box, loaded with catalyst, co-catalyst and solvent (toluene unless otherwise stated) that had previously been dried over sodium and degassed prior to storage in an ampoule in the glove box over a potassium mirror. The autoclave was assembled whilst in the glove box and closed off before removal. After attaching to the rig, the autoclave was pressurised with ethylene to ca 8 bar. After one hour the autoclave was sealed off and the polymerisation stopped. Polymer formed was isolated via filtration over a sintered glass funnel and then washed with copious amounts of acidified methanol and then acetone before drying in an oven overnight. In the case of the polymer formed from the reaction using [Ta(COT")Me_3] (Example 41) the polymer was precipitated from the toluene solution using acidified methanol, Solvent requirements for polymerisation studies were typically in the range of 100–120 ml.

Preparation of MAO—to finely ground [$Al_2(SO_4)_3$ $16H_2O$] (37 g, 60 mmol) suspended in toluene (500 ml) in a 1-liter Schlenk type round bottomed flask and cooled to 0° C. under an atmosphere of argon was added trimethylaluminium as a solution in hexane (290 ml, 2.0M, 580 mmol) dropwise over two hours. After the addition was complete the reaction mixture was heated to ca 40° C. for five hours. Excess pressure was released via a mercury bubbler. After this time the mixture was allowed to stir overnight at room temperature. The reaction mixture was then filtered through celite and the colourless filtrates reduced in vacuo to dryness to afford the product as a highly air sensitive white glassy solid. Yield 8 g, 35%.

The results are given below in Table 3 and clearly show the suitability of the complexes according to the present invention as polymerisation catalysts.

TABLE 3

| Example | Complex | Zr | Al | Start Pressure (bar)(a) | Mass of Polyethylene (g) |
|---|---|---|---|---|---|
| 37 | $Cp_2ZrCl_2$ | 1 | 740 | 9.69 | 3.73 |
| 38 | (COT")ZrCpCl | 1 | 1700 | 9.72 | 4.5 |
| 39 | (COT")ZrCpCl | 1 | 850 | 9.70 | 3.5 |
| 40 | (COT")ZrCp*Cl | 1 | 800 | 10.42 | 1.28 |

TABLE 3-continued

| Example | Complex | Zr | Al | Start Pressure (bar)(a) | Mass of Polyethylene (g) |
|---|---|---|---|---|---|
| 41 | (COT")TaMe₃ | 1 | 1000 | 9.67 | 1.85 |
| 42 | (COT")HfCpCl | 1 | 670 | 9.89 | 3.1 |

I claim:

1. A process for the polymerisation of olefins comprising contacting at least one olefin monomer with a catalyst composition comprising a transition metal complex having the formula I or II:

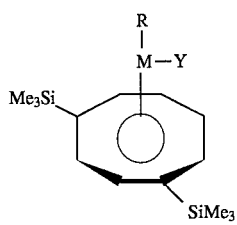

I

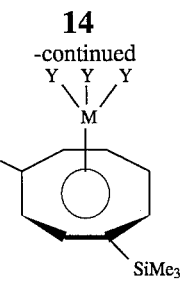

II wherein Y is halide, hydride or a hydrocarbyl group having 1 to 20 carbon atoms and may be the same or different, R is an unsubstituted or substituted cyclopentadienyl ring, and in Formula I M or Zr, Ti, or Hf and in Formula II M is tantalum, vanadium or niobium and (B) an organometallic compound of a metal from Group IA, IIA, IIB, or IIIB of the periodic Table.

2. A process as defined in claim 1 wherein said organometallic compound (B) is an aluminoxane.

3. A process according to claim 1 carried out in the gas phase.

4. A process according to claim 1 wherein the catalyst composition is prepolymerized.

* * * * *

UNITED STATES PATENT AND TRADEMARK OFFICE
CERTIFICATE OF CORRECTION

PATENT NO. : 5,548,044
DATED : August 20, 1996
INVENTOR(S) : Frederick G.N. Cloke It is certified that error appears in the above-indentified patent and that said Letters Patent is hereby corrected as shown below:

Example 17, col. 8, l. 54, correct the formula to read --COT"CpZrCl--

Example 18, col. 9, l. 7, in the formula "CI" should read --Cl--

Col. 12, l. 40, there should be a period (.) not a comma (,) after the word "methanol."

Col. 13, Claim 1, line 3, after "comprising" and before "a" insert --(A)--

Signed and Sealed this

Eleventh Day of February, 1997

Attest:

BRUCE LEHMAN

Attesting Officer       Commissioner of Patents and Trademarks

UNITED STATES PATENT AND TRADEMARK OFFICE
Certificate

Patent No. 5,548,044                                                                               Patented: August 20, 1996

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Frederick G. N. Cloke, Bringhton, England; and Stephen C. P. Joseph, Warwickshire, England.

Signed and Sealed this Fifteenth Day of December, 1998.

*JEFFREY T. SMITH*
*Supervisory Patent Examiner*
Art Unit 1713